United States Patent [19]

Brockbank

[11] Patent Number: 5,131,850
[45] Date of Patent: Jul. 21, 1992

[54] METHOD FOR CRYOPRESERVING MUSCULOSKELETAL TISSUES

[75] Inventor: Kelvin G. M. Brockbank, Marietta, Ga.

[73] Assignee: Cryolife, Inc., Marietta, Ga.

[21] Appl. No.: 431,153

[22] Filed: Nov. 3, 1989

[51] Int. Cl.⁵ .............................................. A01N 1/02
[52] U.S. Cl. .......................................... 435/1; 62/62; 435/2
[58] Field of Search ................... 62/62; 514/54; 435/1, 435/2; 436/8–18; 623/16

[56] References Cited

U.S. PATENT DOCUMENTS

| | | | |
|---|---|---|---|
| 3,033,662 | 2/1967 | Moline et al. | 62/62 |
| 3,444,039 | 5/1969 | Rajamannan | 435/2 |
| 4,486,416 | 12/1984 | Soll et al. | 514/54 |
| 4,800,429 | 11/1989 | Stone | 623/16 |
| 4,959,319 | 9/1990 | Skelnik et al. | 435/240.2 |

OTHER PUBLICATIONS

Vasseur et al., Clinical Orthopedics and Related Research, 219, pp. 268–277 (1987).
Frank et al., "Viability of Ligaments After Freezing: An Experimental Study in a Rabbit Model", Journal of Orthopaedic Research, 6:95–102 (1988).
Arnoczky et al., "The Effect of Cryopreservation on Canine Menisci: A Biochemical, Morphologic, and Biomechanical Evaluation", J. of Orthopaedic Research, (1988).
"Meniscal Transplantation in Goats: An Experimental Study", E. M. Keating, M.D., Center for Hip and Knee Surgery, 34th Annual Meeting, Orthopaedic Research Society, Feb. 1–4, 1988.
Schachar et al., "Investigations of Low-Temperature Storage of Articular Cartilage for Transplantation", Clinical Orthopaedics, Jul. 1986, vol. 208, pp. 146–150.
Fu et al., "The Science of Anterior Cruciate Ligament Implants—1989", American Academy of Orthopaedic Surgeons 56th Annual Meeting, (1989).
Nikolaou et al., "Anterior Cruciate Ligament Allograft Transplantation" Long-Term Function, Histology, Revascularization, and Operative Technique, pp. 348–360, The American Journal of Sports Medicine, vol. 14, No. 5 (1986).

*Primary Examiner*—Sam Rosen
*Attorney, Agent, or Firm*—Cushman, Darby & Cushman

[57] ABSTRACT

Disclosed herein is a method for cryopreserving musculoskeletal tissues, such as ligaments, tendons and cartilage, by placing such tissue in contact with a composition containing a cryopreserving agent comprising a cell-penetrating organic solute, which is preferably dimethylsulfoxide, and a glycosaminoglycan, which is preferably chondroitin sulphate, in an amount sufficient to cryopreserve the musculoskeletal tissue. The addition of a glycosaminoglycan to a cryopreserving agent comprising a cell-penetrating organic solute permits a broad range of cooling rates to be employed, rather than the very narrow ranges which are employed using a cryopreserving agent comprising a cell-penetrating organic solvent without the glycosaminoglycan. Also disclosed are a freezing schedule designed to maximize retention of tissue cell viability and biomechanical properties during and after the freezing process, and a thawing schedule which maximizes cell viability.

9 Claims, 3 Drawing Sheets

METHOD FOR CRYOPRESERVING MUSCULOSKELETAL TISSUES

BACKGROUND OF THE INVENTION

1. Field of the Invention

The present invention relates to a method for cryopreserving musculoskeletal tissues and, in particular, to a method for cryopreserving musculoskeletal tissues by placing such tissue in contact with a composition containing a cryopreserving agent comprising a cell-penetrating organic solute and a glycosaminoglycan, in an amount sufficient to cryopreserve the musculoskeletal tissue.

2 Background Information

There is an increasing demand for musculoskeletal transplants. For example, there were approximately 600,000 knee ligament injuries worldwide in 1986. Of these, 10% or 60,000 were treated with surgical implants. The current available implants fall into the following general categories: (a) synthetic prosthetics, (b) chemically treated xenograft bioprostheses, and (c) human allograft tissue transplants. A variety of synthetic ligaments have been investigated since the early 1970s. However, none are currently approved for primary reconstruction. Xenografts have problems associated with the toxicity of the chemical fixatives, cross species antigenicity and long-term (as well as short-term) biomechanical integrity. Also, non-orthotopically placed autografts have the drawback that there is additional morbidity created at the graft harvest site. Both allografts and autografts used in ligament reconstruction have primarily consisted of patellar tendon, fascia lata, Achilles tendon, and semitendinosus.

Investigators have generally agreed that fresh, viable tissue gives improved performance over old or dead tissue; and viable human tissue exceeds the useful performance of xenograft materials. However, tissue remains alive for only short periods of time after removal from a donor. The fibroblasts, fibrocytes, and chondrocytes, which are the major cellular constituent of musculoskeletal tissues, remain viable for, at most, several days in a refrigerated life-sustaining media. In order to bank ligamentous tissues destined for transplantation, methods for viable tissue storage are required. The availability of viable ligamentous tissues will permit matching to recipient immunological and size requirements.

Prior art techniques, such as freeze drying, glutaraldehyde fixation and mechanical freezing, combined with the sterilization techniques of irradiation, ethylene oxide, and antibiotics, do not maintain cell viability and generally lead to early graft failure.

The long term storage of cells and tissues became possible after the discovery in 1949, by Polge, Smith and Parks, that glycerol could be used to protect cells from injury due to freezing. With the advent of low temperature biology, workers in medical and biological fields have been seeking better ways to maintain the viability of frozen donor cells or tissues.

The essential makeup of individual cells affects the specifics of the cryopreservation process. A particular type of tissue is often predominantly composed of a specific cell type. The cell is often specialized with respect to the nature of the tissue it makes up. Different cells have different characteristics, such as heat and mass transfer properties based on the cell density and molecular make up. These properties affect the specifics of the cryopreservation process.

The requirements for successful cryopreservation are twofold. First, the harvested tissue must be frozen to a sufficiently low temperature so as to cause cessation of all metabolic activity of the cell, without destroying the cell. Second, the cryopreservation and thawing technique must have minimal effects on tissue cell viability and functions. Furthermore, the shelf-life of the cryopreserved tissues should be infinite. The life expectancy of tissues stored in liquid nitrogen can be measured in thousands of years.

Previous to now, there has not been available a method for the cryopreservation of musculoskeletal tissues that adequately meets the above requirements. Thus, a new method for the cryopreservation of musculoskeletal tissues is needed.

SUMMARY INVENTION

It is a general object of the present invention to provide a method for preserving living, biochemically functional musculoskeletal tissues, including mammalian musculoskeletal tissues.

It is another object of the present invention to provide a method for cryopreserving musculoskeletal tissues which permits a broad range of cooling rates to be employed.

It is still another object of the present invention to provide a method for cryopreserving musculoskeletal tissues which allows for rapid thawing of the tissues, while maintaining maximum cell viability and biomechanical function.

It is yet another object of the present invention to provide a cryopreserved living musculoskeletal tissue that is suitable for transplantation after long-term storage at temperatures below $-130°$ C.

Further objects and advantages of the invention will be clear to one skilled in the art from a reading of the description that follows.

The present invention is directed to a method for cryopreserving musculoskeletal tissues, such as ligaments, tendons and cartilage, by placing such tissue in contact with a composition containing, in a buffered physiological solution, a cryopreserving agent comprising a cell-penetrating organic solute and a glycosaminoglycan, in an amount sufficient to cryopreserve the musculoskeletal tissue. Any suitable glycosaminoglycan can be used, although chondroitin sulphate is preferred. The cell-penetrating organic solute is preferably dimethylsulfoxide (DMSO), although other suitable cell-penetrating organic solutes can be used.

In one embodiment, the composition comprises 0.5 to 100 ml of a buffered physiological solution; a glycosaminoglycan having a concentration of from about 1% to about 10%, preferably from about 2.5% to about 5%, and more preferably about 2.5%; and a cell-penetrating organic solute in a concentration of from about 0.5M to about 3M, preferably about 0.75M to about 1.5M, and more preferably about 1M. A serum of any species can optionally be included in the composition in a concentration of from about 1% to about 30%, and preferably about 10%.

The addition of a glycosaminoglycan to a cryopreserving agent comprising a cell-penetrating organic solute permits a broad range of cooling rates to be employed, rather than the very narrow ranges which are employed using a cryopreserving agent comprising a cell-penetrating organic solvent without the glycosaminoglycan. According to the present invention, the overall cooling rate during cryopreservation of musculoskeletal tissue from 0° C. to −80° C. is preferably between −0.4° C. and −3° C. per minute, although slower cooling rates in the range of from −0.1° C. to −0.3° C. can also be used. This broad range for optimal cooling of the musculoskeletal tissue during cryopreservation enhances the preservation, after thawing, of the two important components of the tissue: (1) the fibroblasts, fibrocytes and chondrocytes which maintain and produce the extracellular matrix components, which are responsible for the tissue's long term biomechanical properties, and (2) the structure and immediate biomechanical properties of the musculoskeletal tissue.

DETAILED DESCRIPTION OF THE INVENTION

Figure 1:
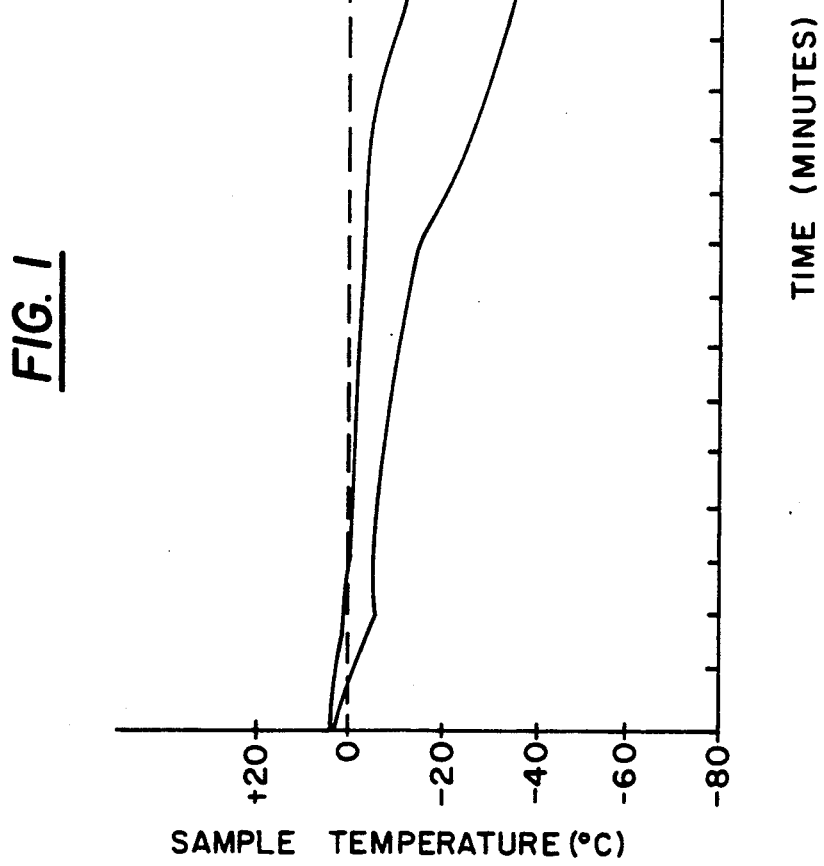
FIG. 1. The range for optimal cooling of musculoskeletal tissue during cryopreservation is illustrated by this Figure. The range is derived from pooled experimental sample cooling curves which yielded viable tissue.

The present invention is directed to a method of cryopreserving musculoskeletal tissues, including, but not limited to ligaments, tendons and cartilage, comprising placing such tissue in contact with a composition containing, in a buffered physiological solution, a cryopreserving agent comprising a cell-penetrating organic solute and a glycosaminoglycan, in an amount sufficient to cryopreserve the musculoskeletal tissue. The musculoskeletal tissue can be mammalian, or more particularly, human tissue.

The addition of a glycosaminoglycan to a cryopreserving agent comprising a cell-penetrating organic solute permits the use of a broad range of cooling rates, rather than the very narrow ranges which are employed using a cryopreserving agent comprising a cell-penetrating organic solvent without the glycosaminoglycan. The method of the present invention has the additional advantage of allowing for rapid thawing of living, biochemically functional musculoskeletal tissues, while maintaining maximum cell viability and biomechanical function. In addition, the method of the present invention provides a cryopreserved living musculoskeletal tissue that is suitable for transplantation after long-term storage at temperatures below −130° C.

The glycosaminoglycan of the present invention is preferably chondroitin sulphate, although any suitable glycosaminoglycan can be used, such as hyaluronic acid, dermatan sulphate, heparin sulphate and keratan sulphate.

The cell-penetrating organic solute is preferably DMSO, although other suitable cell-penetrating organic solutes can be used, such as polyalcohols (for example, ethylene glycol, propylene glycol, glycerol and butane diol); and alkyl sulphoxides (for example, methyl ethyl sulphoxide, diethylsulphoxide, dibutylsulphoxide, methylbutyl sulphoxide, and ethylbutylsulphoxide).

The cryopreserving agent is added in solution to the musculoskeletal tissue to protect the cells during freezing. Any buffered physiological solution can be used in practicing the present invention, such as tissue culture media and simple buffered salt solutions. Tissue culture media is the preferred buffered physiological solution, with Dulbecco's Modified Eagle Medium (DMEM) being the preferred tissue culture medium.

In one embodiment, the composition comprises 0.5 to 100 ml of buffered physiological solution; a glycosaminoglycan having a concentration of from about 1% to about 10%, preferably from about 2.5% to about 5%, and more preferably about 2.5%; and a cell-penetrating organic solute in a concentration of from about 0.5M to about 3M, preferably about 0.75M to 1.5M, and more preferably about 1M. A serum of any species can optionally be included in a concentration of from about 1% to about 30%, and preferably about 10%. The volume of solution used is easily determined by one skilled in the art, and is dependent upon the size of the tissue to be preserved.

In another embodiment, the composition comprises 0.5 to 100 ml of DMEM; fetal calf serum (FCS) in a concentration of from about 1% to about 30%, preferably about 10%; chondroitin sulphate having a concentration of from about 1% to about 10%, preferably from about 2.5% to about 5%, and preferably about 2.5%; and DMSO in a concentration of from about 0.5M to about 3M, preferably about 0.75M to about 1.5M, and more preferably about 1M.

The organic solute is added either in at least one step of 1M or, preferably, in three steps of .25M, .5M and 1M titrations at 4° C. The increase in molarity of the cell-penetrating organic solute is preferably gradual. The cell-penetrating organic solute may be added at higher temperatures, but timing becomes far more critical and toxicity may result in some tissues. Use of a cell-penetrating organic solute without a glycosaminoglycan results in a narrower optimum cooling range.

All procurement of musculoskeletal tissue is performed under sterile conditions. The antibiotic used according to the present invention is microbially effective, while sparing the cells which are important for long-term tissue maintenance.

Cryopreservation is preferably initiated within 20 to 60 minutes after addition of the cryopreserving agent, and more preferably, within 30 to 40 minutes. The water to ice phase change is initiated at −2° to −6° C. by a burst of liquid nitrogen, sterile ice crystal, or by vibration. The overall cooling rate from 0° C. to −80° C. is preferably between −0.4° C. and −3° C. per minute (see FIG. 1). Slower cooling rates in the range of from −0.1° C. to −0.3° C. are also acceptable, although slower cooling rates may lead to excessive osmotic dehydration of the cells. Cooling rates between −3° C. and −30° C. give progressively less viability. Cooling rates more rapid than −30° C. per minute are unacceptable.

Once the musculoskeletal tissue has been cooled to −80° C., it is transferred to a low temperature (−130° C. or lower) storage unit. Storage at warmer temperatures may result in migratory ice recrystallization and biochemical degradation, which can reduce tissue viability.

Figure 2:
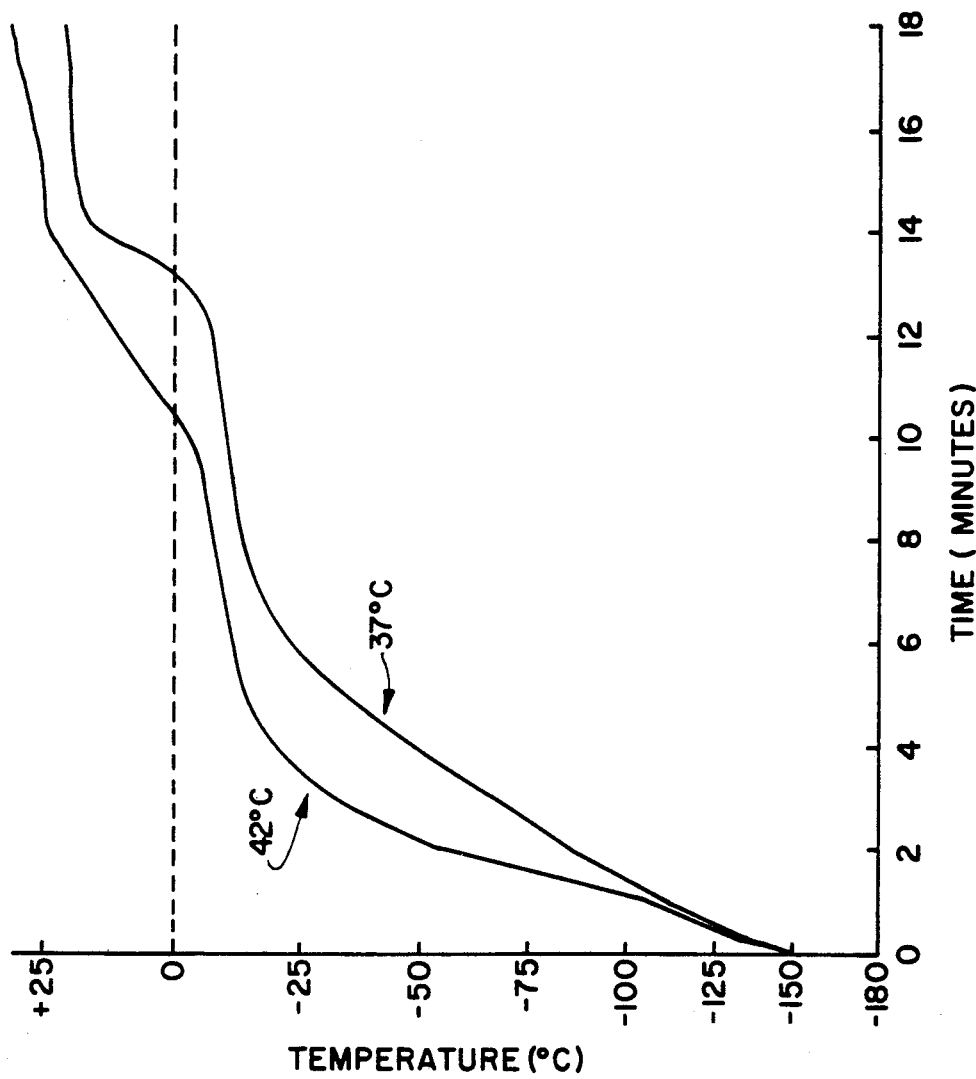
FIG. 2. Warming curves obtained during thawing of samples in either a 42° C. (3 liter) water bath without continuous heating or a 37° C. (6 liter) temperature controlled water bath are illustrated by this Figure. Using either thawing method, the tissue is thawed in 10-14 minutes and the tissue maintains viability.

The tissue must be thawed prior to transplantation. Although any suitable method can be used, the tissue is preferably thawed by placing the frozen tissue in a bath of warm liquid, preferably at 4° C. to 42° C., and more preferably at 37° C. to 42° C. The volume of liquid employed in the bath may vary considerably if a temperature-controlled bath is employed. If a temperature-controlled bath is not employed, the volume of liquid employed should be at least 2 liters. Warming rate curves for these two methods are shown in FIG. 2. The package containing the tissue is completely submersed in the liquid bath, until such time that inspection of the package reveals that no ice is present. The tissue should then be removed using a sterile technique and placed in 0.5M mannitol and 10% FCS in DMEM for 2 to 5 minutes. Any non-cell membrane permeable biocompatible sugar, polyol or other organic solute can be substituted for mannitol, such as sucrose, sorbitol, trehalose, fructose, glucose, raffinose, maltose, xylitol, amino acids or the like.

The dilution of DMSO concentration by the biocompatible sugar solution is preferably in decreasing steps of no more than half the molarity of the previous step. Thus, if the original DMSO concentration is 2M, the first dilution step would employ 1M sugar. In this instance, 1M DMSO is preferred, so the first step employs ½M sugar, and is followed by 5 minute steps with 50 ml of solution with ¼M sugar, and finally 50 ml of solution with zero molar sugar. The tissue is then ready for transplantation.

The following non-limiting Examples, which are illustrative of the present invention, demonstrate the preservation of musculoskeletal tissue viability and biomechanical properties using the cryopreservation method and composition of the invention.

EXAMPLE 1

This Example illustrates the discovery that addition of chondroitin sulphate to a cryopreservation solution containing DMSO broadens the optimum cooling rate range.

A. In Vitro Cryopreservation of Anterior Cruciate Ligament Cells

Anterior cruciate ligament (ACL) cells were cultured from explants of ACL in vitro. Once adequate numbers of cells were obtained, cryopreservation experiments were initiated. The method consisted of growing the fibroblasts to low confluence in 4 well multidishes (Nunclon, Denmark). The cultures were always fed with fresh culture medium (DMEM) containing 10% fetal calf serum the day before experiments, in order to ensure that the cells were in optimal metabolic condition. The cultures were frozen either without cryoprotectants (control), with dimethylsulphoxide (DMSO), or with a proprietary combination of cryoprotectants including chondroitin sulphate and DMSO (CryoLife solution) using a Cryomed control rate freezer. The results are shown below in Table 1.

TABLE 1

| Cryopreservation of ACL-derived fibroblasts | | | | |
|---|---|---|---|---|
| Cooling Rate (C) | # of Expts. | Cryolife Soln | DMSO | Control** |
| 30 | 4 | 371* | 117 | 73 |
| 10 | 4 | 409* | 303 | 74 |
| 3 | 5 | 698* | 381 | 79 |
| 0.5 | 5 | 500* | 397 | 74 |

The data is presented as the mean of 4 or 5 experiments,
*= $P < .05$ by ANOVA one way analysis of variance.
**Viability expressed as DPM, assay desribed below.

The above results indicate a significant enhancement at all cooling rates tested for the CryoLife solution containing both chondroitin sulphate and DMSO, in contrast to DMSO alone. Control values are without any cryoprotection.

B. Tritiated Glycine Labelling of Cells

Plates containing cells were thawed a few at a time by floating them in a 37° C. water bath until the ice melted completely. The plates were then quickly cleaned, ~0.3 ml of DMEM+10% FCS were added carefully along the sides of the wells, allowed to equilibrate ~1 minute following which another 0.3 ml medium was added and allow to equilibrate. Next, all medium was removed, −0.3 ml of fresh medium/well were added, and the plates were placed in a $CO_2$, incubator for ~24 hours.

The next day a serum free medium was prepared with the following composition:
DMEM (no HEPES): 500 ml
Gentamicin: 2.5 ml (25 mg)
Ascorbic Acid: 75 mg
Glucose: 25 mg
Sodium Pyruvate: 0.55 g
The medium was filter sterilized after mixing well.

The plates were taken from the incubator and the medium was removed. 0.3 ml of serum free medium/well was added and the plates placed back in the incubator for 1 hour. After 1 hour the plates were removed from the incubator and in small batches, the medium was removed and 0.3 ml of the labelling medium (8μCi $^3$H-glycine)/well was added (with pipetman). The plates were then placed back in the incubator for another 24 hours.

The next day the plates were removed again from the incubator, the medium removed and each well washed 3 times with PBS. After the last wash as much liquid as possible was removed, and 0.5 ml of PBS/well was added and frozen to ~20° C. to disrupt the cells.

The plates were removed from the freezer, and thawed at room temperature or 37° C., as desired. The cells were viewed with a microscope to determine whether or not all cells were detached from the bottom of the wells—if not, the plates were frozen and thawed again. When the cells were up, the 0.5 ml in each well was removed to a pre-labelled micro tube using a pipetman and by aspirating the liquid up and down vigorously. Each well was washed twice more with 0.25 ml of PBS and the washes were added to the initial 0.5 ml resulting in a total of 1.0 ml for each well. Each tube was sonicated one time for about 20 seconds (the tubes were kept on ice after sonication), then 100 μl of each were pipetted onto a glass fiber filter paper circle. The samples were allowed to dry on filter papers, then each was placed into a 20 ml glass scintillation vial. To each vial 2 ml of ice-cold 10% TCA were added, then all samples were placed in the refrigerator for a minimum time period of 15 minutes or a maximum time period of over the weekend. The TCA was then aspirated off. 3 ml of ice-cold alcohol was added and aspirated for a total of 6 washes with alcohol. The samples were next washed two times with ice-cold ether. The samples were then allowed to dry completely in the hood. Each filter paper was wetted with ~130 μl of water. 1 ml of Protosol/vial was added and vortexed vigorously. 10 ml of Scintillation cocktail and then 100 μl of Glacial acetic acid were added to each vial, following which the vial was capped and swirled. The samples were allowed to dark adapt for 30 minutes before counting in the scintillation counter. The counts were expressed as radioactive disintegrations per minute (DPM).

EXAMPLE 2

This Example illustrates the viability of cryopreserved anterior cruciate ligaments, patellar tendons and menisci derived from dogs, primates (*Macacca nemistrina*), and humans after cryopreservation and thawing according to the method of the invention.

Anterior cruciate ligaments, patellar tendons and menisci were obtained from human tissue donors, *Macacca nemistrina* and using the sterile dissection technique. The tissue was incubated at 37° C. in 5% CO, for 4 hours in a mixture of DMEM containing 12 μg/ml of the antibiotic, Imipenem.

After 4 hours the tissue was removed from the incubation mixture and placed into a plastic freezing bag into which there was added 35 ml of ice cold medium, consisting of:
DMEM (with 25 mM HEPES),
10% fetal calf serum,
1M DMSO, and
2.5% chondroitin sulfate.

The plastic bag was sealed and any excess length was cut off. The plastic bag was then enclosed in an outer foil pouch, which was then sealed. Bags were kept on ice for 30 minutes and then frozen at a rate of 0.5° C. per minute in a programmable cooling chamber according to the following procedure:
Cool chamber to 4° C.
2° C./min to −2° C. sample
30° C./min to −100° C. chamber
20° C./min to −85° C. chamber
3 minute hold −85° C.
10° C./min to −30° C. chamber
1 minute hold −30° C.
0 01° C./min to −20° C. sample
0.5° C./min to −80° C. sample When the sample reached −80° C., it was transferred to liquid nitrogen (−196° C.) storage. The tissue was kept in liquid nitrogen storage until needed.

Thawing was then performed by placing the unopened foil bag in a large basin of warm (37°–42° C.) water for 10 minutes. The foil bag was cut open, and the inner plastic bag was removed in a sterile fashion. The plastic bag was cut open with sterile scissors and the contents of the plastic bag emptied into a sterile container. The tissue was removed from the container and placed into a sterile 50 ml tube to which had been added 25 ml of Solution A (0.5M mannitol in DMEM). The tissue was then allowed to equilibrate for 2 minutes, after which it was removed from the tube and placed in a second 50 ml tube to which had been added 25 ml of Solution A and 25 ml of Solution B (DMEM). The tissue was then allowed to equilibrate for 2 minutes, following which it was removed from the tube and placed in a third 50 ml tube containing only Solution B for 2 minutes. The tissue was then ready for transplantation or viability assay.

Viability was determined by incubating approximately 1 $mm^3$ pieces of tissue in 0.5 ml DMEM containing 16 μCi/ml$^3$H-glycine for 48 hours at 37° C. Upon completion of the incubation, the radio-labelling medium was decanted from the tube and the tissue washed twice with phosphate buffered saline (PBS). PBS was added and the tissue allowed to sit for 30 minutes. The PBS was then removed and more PBS added, after which the tissue was allowed to incubate overnight at 4° C.

The next day, PBS was decanted off of the tissue and the tissue placed into 15×100 mm glass tubes. The tissue was then washed for in alcohol, following which it was washed for 15 minutes with ether. The ether was removed and the tissue allowed to dry for at least one hour. The tissue from each tube was then weighed and the weight recorded. All tissue was then placed into clean 12×15 mm glass tubes.

200 μl $H_2O$ were added to each tube and the tissue allowed to rehydrate for 30 minutes to 1 hour. 500 μl of 1M NaOH were added to each tube and the tubes placed in a heating block at 60° C. for 30 minutes. Samples were pipetted into microtubes and sonicated twice for 20 seconds each time, following which the samples were centrifuged in a microfuge for 2 minutes at 12,500 g.

100 μl of each sample were applied to glass fiber filter discs which were then allowed to dry for at least one hour. The filter discs were moved to glass scintillation vials and 2 ml ice cold 10% trichloroacetic acid (TCA) were added to each vial, following which the vials were refrigerated for a minimum of 30 minutes. TCA was then removed and the tissue washed four times with 3 ml ice cold alcohol, following which it was washed twice with 3 ml ice cold ether. The filter discs were allowed to dry for at least one hour. The samples next were rehydrated by adding 130 μl $H_2O$ to each filter disc. 1 ml Protosol was then added to each vial, following which the vials were vortexed vigorously. 10 ml scintillation fluid and 100 μl glacial acetic acid were added. The vials were transferred into racks, and the racks placed in a scintillation counter and allowed to dark adapt for 30 minutes before counting. Each vial was counted for 5 minutes.

Data were accumulated as disintegrations per minute (DPM) and corrected to DPM/mg dry weight of tissue. The mean viability of the tissue samples in percent of untreated control tissue is presented in Table 2 below. Viability was assessed by quantitation of $^3$H-glycine incorporated into proteins during a 48 hour incubation at 37° C.

TABLE 2

| Tissue Type | Number of Samples | Species | Result (%) |
| --- | --- | --- | --- |
| ACL[1] | 6 | Dog | 80 |
| PT[2] | 5 | Dog | 59 |
| M[3] | 4 | Dog | 41 |
| ACL[1] | 2 | Primate | 99 |
| PT[2] | 4 | Primate | 46 |
| M[3] | 5 | Primate | 59 |
| PCL[4] | 9 | Human | 61 |
| ACL[1] | 8 | Human | 66 |
| PT[2] | 4 | Human | 45 |

TABLE 2-continued

| Tissue Type | Number of Samples | Species | Result (%) |
|---|---|---|---|
| M[3] | 22 | Human | 32 |

[1]ACL = Anterior cruciate ligament
[2]PT = Patellar tendon
[3]M = Meniscus
[4]PCL = Posterior cruciate ligament The above data demonstrate that the cryopreservation method of the invention maintains a high level of viability for cruciate ligaments and an intermediate level for patellar tendons. Animal transplantation studies have revealed that anterior cruciate ligaments and menisci retain similar levels of viability after 3 months in dogs.

EXAMPLE 3

Non-destructive, constant strain rate, tensile tests were performed on canine anterior cruciate ligaments, prior to and following cryopreservation according to the method of the invention in order to demonstrate the preservation of optimal biomechanical function.

All tests were conducted on a tensile testing apparatus consisting of an environmental test chamber, a force actuater, a force transducer and displacement transducer, all interfaced to a computerized control system. The tests were software controlled and the data recorded by an electronic data acquisition system.

Because of the degree of variation between ligaments from different individuals, and even between contralateral ligaments from a single individual, the inventors chose to design a nondestructive test procedure so that each ligament could serve as its own control. The following procedure was performed on each test ligament before and after cryopreservation and thawing. Cryopreservation and thawing were performed as indicated in Example 2.

The bone-ligament-bone complex was mounted in specially designed receptacles which held the ligament in the orientation corresponding to 45° of flexion. Forty-five degrees of flexion is reported most commonly in the literature as the angle at which both the anteromedial and the posterolateral bundles are under approximately equal tension. After the test ligament was loaded in the testing apparatus, the chamber was filled with sterile 37° C. DMEM. The DMEM was maintained at 37° C. by circulation through a heat exchanger immersed in a constant temperature water bath.

The mechanical testing began with a 10 cycle preconditioning at a 1% per second strain rate between 0 lb. and 45 lbs using the Fortran Program UNAXCR. After this, the test cycle was recorded. A one hour recovery period was allowed before the next test to ensure the same starting point in the stress-strain history.

The ligament was then preconditioned between the same forces (0 lb to 45 lbs) at a 50% per second strain rate. Using the Fortran program, UNAXCR, the test cycle was recorded and immediately followed by a relaxation test beginning at 45 lbs. This test was recorded for 30 minutes, after which the ligament was brought back to the resting position of zero tension and allowed to recover for an hour.

The next preconditioning was between 0 lb and 20 lbs at 50% per second, after which a relaxation test beginning at 20 lb was recorded for 30 minutes.

After allowing recovery as before, the ligament was again preconditioned at 50% per second between 0 lb and 45 lbs, followed by a 5 lb creep test which was recorded for 30 minutes.

Figure 3:
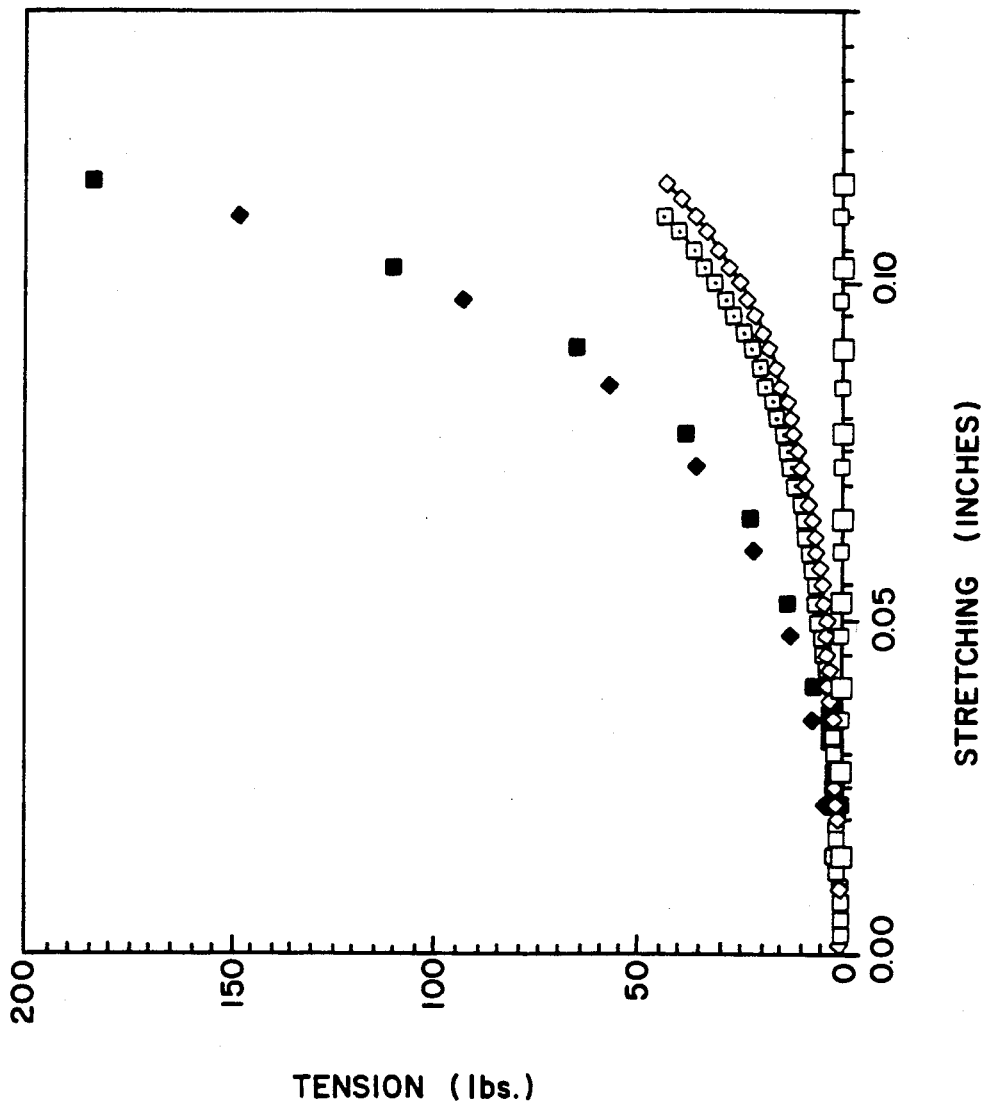
FIG. 3. The data for nondestructive, constant strain rate, tensile tests on canine cranial cruciate ligaments, both prior to and following cryopreservation by the disclosed process, are shown in this Figure by the depicted Force vs. Elongation relationships. Eighteen ligaments were tested, with the data from each fresh ligament serving as its own control for the data associated with that same ligament following frozen storage. The mean values of elongation for a given applied tensile force, for both the fresh and cryopreserved tissue, fall well within the interval defined by one standard deviation about either mean.

Eighteen ligaments were tested with the data from each fresh ligament serving as its own control for the data associated with that same ligament following cryopreservation. The Force vs. Elongation relationships depicted in FIG. 3 give the data for nondestructive, constant strain rate, tensile tests on canine anterior cruciate ligaments, both prior to and following cryopreservation by the above-described process. The mean values of elongation for each applied tensile force, for both the fresh and cryopreserved tissue, fell well within the interval defined by one standard deviation about either mean. Therefore, there is no significant difference.

EXAMPLE 4

Tests were performed to assess the short-term clinical function, histology, and protein-synthesizing capabilities of viably cryopreserved canine anterior cruciate ligament allografts.

Initial experiments employing ($^3$H)glycine incorporation into proteins indicated that anterior cruciate ligaments could be retrieved up to 6 hours postmortem at room temperature and that they could tolerate at least 24 additional hours in procurement solution on ice. Cryopreservation was performed as indicated in Example 2 using a control-rate freezer, and the anterior cruciate ligaments with bone plugs attached were stored in liquid or vapor phase nitrogen for at least 24 hours prior to use. Thawing was accomplished by immersion in a 37° C. to 42° C. water bath and cryopreserving agents were diluted out in three steps. Six anterior cruciate ligament allografts were harvested from adult greyhounds and cryopreserved for transplantation; 6 greyhounds were matched on the basis of age, sex, weight, and hindquarter dimensions to serve as transplant recipients in the study. Surgical implantation of the allografts was accomplished by a double tunnel technique for orthotopic graft placement. Following surgery, the dogs were housed, without immobilizing bandages, in hospital cages for 4 weeks, at which time they were moved to indoor/outdoor runs for the remainder of the study.

Clinical assessment of the 6 transplant recipients at 3 months revealed that the mean gait and anterior drawer sign were 1 and 1.2 units, respectively, on a standard 4 point scale in which 4 is the worst score possible. Comparison of the graft and control anterior cruciate ligament viabilities using ($^3$H)glycine incorporation demonstrated that the grafted anterior cruciate ligaments had a mean of 88% protein synthesis relative to controls. Histologically, the bone plugs were well incorporated at the insertion sites by newly formed bone. The ligaments generally exhibited a mild fibroplasia with a small central acellular region exhibiting necrosis and a varying degree of cartilaginous metaplasia. The synovial membrane was normocellular and vascularized and revascularization had occurred at each end of the ligament. The collagen fibers were generally well oriented and fragmentation was not observed. Lymphocytic infiltration was very slight in all grafts as assessed by routine histology and synovial fluid cytology. The short-term results of this study are thus very encouraging and are expected to stimulate interest in long-term evaluation of cryopreserved anterior cruciate ligament allografts.

The invention having been described, it will be appreciated by those skilled in the art, that various modifications can be made within the scope of the following claims.

I claim:

1. A method of cryopreserving musculoskeletal tissue comprising placing the tissue in contact with a cryopreserving agent comprising a cell-penetrating organic solute and a glycosaminoglycan, in an amount sufficient to cryopreserve the musculoskeletal tissue, and maintaining the musculoskeletal tissue in contact with the cryopreserving agent in a frozen state.

2. The method of claim 1, wherein the musculoskeletal tissue is placed in contact with the cryopreserving agent which comprises chondroitin sulphate as the glycosaminoglycan.

3. The method of claim 1, wherein the musculoskeletal tissue is placed in contact with the cryopreserving agent which comprises the glycosaminoglycan in a concentration of from about 1% to about 10%.

4. The method of claim 3, wherein the musculosketal tissue is placed in contact with the cryopreserving agent which comprises the glycosaminoglycan in a concentration of from about 2.5% to about 5%.

5. The method of claim 4, wherein the musculoskeletal tissue is placed in contact with the cryopreserving agent which comprises the glycosaminoglycan in a concentration of about 2.5%.

6. The method of claim 1, wherein the musculoskeletal tissue is placed in contact with the cryopreserving agent which comprises dimethylsulphoxide as the cell-penetrating organic solute.

7. The method of claim 1, wherein the musculoskeletal tissue is placed in contact with the cryopreserving agent which comprises the cell-penetrating organic solute in a concentration of from about 0.5M to about 3M.

8. The method of claim 7, wherein the musculoskeletal tissue is placed in contact with the cryopreserving agent which comprises the cell-penetrating organic solute in a concentration of from about 0.75M to about 1.5M.

9. The method of claim 8, wherein the musculoskeletal tissue is placed in contact with the cryopreserving agent which comprises the cell-penetrating organic solute in a concentration of 1M.

* * * * *